(12) United States Patent
Nacey

(10) Patent No.: US 9,639,663 B1
(45) Date of Patent: *May 2, 2017

(54) VISUAL DISPLAY OF ROOM INFORMATION

(71) Applicant: TeleTracking Technologies, Inc., Pittsburgh, PA (US)

(72) Inventor: Gene E. Nacey, Leechburg, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/281,372

(22) Filed: May 19, 2014

Related U.S. Application Data

(63) Continuation of application No. 10/005,985, filed on Nov. 12, 2001, now Pat. No. 8,732,573, which is a continuation-in-part of application No. 09/567,897, filed on May 10, 2000, now Pat. No. 8,560,580.

(60) Provisional application No. 60/133,524, filed on May 10, 1999.

(51) Int. Cl.
*G06Q 50/22* (2012.01)
*G06Q 50/24* (2012.01)
*G06F 19/00* (2011.01)

(52) U.S. Cl.
CPC .................. *G06F 19/327* (2013.01)

(58) Field of Classification Search
CPC ... A61B 5/1115; A61B 5/7435; A61B 5/6891; A61B 5/002; G06Q 50/24; G06Q 50/22; G06Q 10/06; G06Q 10/02; G06Q 10/087; G06Q 10/06311; G06F 19/327
See application file for complete search history.

(56) References Cited

U.S. PATENT DOCUMENTS

2003/0074222 A1* 4/2003 Rosow et al. .................. 705/2

* cited by examiner

*Primary Examiner* — Maroun Kanaan
(74) *Attorney, Agent, or Firm* — Ference & Associates LLC

(57) ABSTRACT

An embodiment provides a method of graphically displaying room information, including: displaying, on an electronic device, a matrix having a plurality of cells therein, at least one cell displaying hospital room information regarding room availability and patient occupancy in the room; said matrix displaying the plurality of cells in column form; and displaying, responsive to a user interaction with a cell in the matrix of a patient occupied hospital room, an overlay window having secondary room status information therein comprising patient specific information regarding the status of the hospital room.

20 Claims, 4 Drawing Sheets

FIG. 1

VISUAL DISPLAY OF ROOM INFORMATION

CROSS REFERENCE TO RELATED APPLICATIONS

This application is a continuation application of U.S. application Ser. No. 10/005,985, filed Nov. 12, 2001, which is in turn a continuation-in-part application of U.S. application Ser. No. 09/567,897, filed on May 10, 2000, which is a non-provisional of U.S. Application Ser. No. 60/133,524, filed on May 10, 1999, the contents of each prior application are hereby incorporated by reference herein.

FIELD

The present invention relates generally to a hospital communication system and more particularly relates to an apparatus and method to present patient room information to hospital personnel to enhance comprehension of such information.

BACKGROUND

Nurses and other attending staff in a hospital ward or hospital wing work under conditions involving high pressure, stress and long hours. These care givers must remain alert to respond to patient needs, in both emergency and non-emergency situations. Due to economic practicalities and the ever-increasing costs of medical care, it is necessary to make the most efficient use of nurses and staff on call in a hospital ward or hospital wing, particularly at night when nurse and staff levels are maintained at a minimum.

On the other hand, a desire to optimize the efficiency of nurse and staff personnel is of secondary importance relative to the primary objective, that of providing a high level of medical care to a patient. If nurse and staff levels are reduced for the sake of efficiency without any corresponding simplification of duties and responsibilities, the level of patient care will decrease. Therefore, it is desirable to maximize the efficiency of nurses and staff on call in a hospital wing or hospital ward, but to do so in a manner which does not increase the work load or stress levels of these professional care givers nor decrease the level of patient care.

One approach to maximizing the efficiency of nurses and other hospital staff involves providing information needed by these professionals in a location remote from a patient room. For instance, U.S. Pat. No. 5,699,038 to Ulrich et al. discloses a bed status information system of hospital beds which provides remote instantaneous retrieval of unique identification information about the bed and provides status information related to the position of the bed, the configuration of the mattress surface, the status of the safety systems on the bed, and the current state of various patient care systems integrated with the bed. Monitoring of patient information therefore does not require attendance within the room to locally view and interpret various types of information. U.S. Pat. No. 5,867,821 to Ballantyne et al. discloses a method and apparatus for electronically accessing and distributing personal health care information and services in hospitals and homes in which certain information, ranging from patient health record information to patient and operating room monitoring information, is distributed to a nursing station within a hospital.

Providing information to nurses and other hospital staff in a location remote from a patient room creates certain problems. Among the problems is presenting information to the medical professionals in a way that assists them in effectively monitoring the information without increasing their level of stress, which may occur if they feel overwhelmed by the amount of information. A need has thus been recognized in conjunction with responding to the aforementioned problems.

SUMMARY

The present invention, in accordance with at least one presently preferred embodiment, utilizes the capabilities of a computer to graphically display selected information in a manner which conveys the information to hospital staff in a form which aids in comprehension of the information. Specifically, the information is preferably conveyed for multiple patient units through the use of matrix type format. A cell is used to represent each room in patient units being displayed. Components of the cell indicate key considerations for every bed control or admitting department. Additional information may also be displayed by clicking a component of a cell.

Consequently, the present invention broadly contemplates a method whereby hospital room information is visually displayed, thereby aiding hospital staff in comprehending the hospital bed information. An example of hospital staff which could benefit from the present invention includes nurses and the staff in the admissions department and who assign patients to rooms.

In one aspect, an embodiment provides a method of graphically displaying room information, comprising: displaying, on an electronic device, a matrix having a plurality of cells therein, at least one cell displaying hospital room information regarding room availability and patient occupancy in the room; said matrix displaying the plurality of cells in column form; and displaying, responsive to a user interaction with a cell in the matrix of a patient occupied hospital room, an overlay window having secondary room status information therein comprising patient specific information regarding the status of the hospital room.

In another aspect, an embodiment provides an apparatus, comprising: a display device; and a component that interacts with the display device to display room information; the display device displaying a matrix having a plurality of cells therein, at least one cell displaying hospital room information regarding room availability and patient occupancy in the room; said matrix displaying the plurality of cells in column form; and the display device displaying, responsive to a user interaction with a cell in the matrix of a patient occupied hospital room, an overlay window having secondary room status information therein comprising patient specific information regarding the status of the hospital room.

In another aspect, an embodiment provides a program storage device readable by machine, embodying a program of instructions executable by the machine to perform: displaying, on an electronic device, a matrix having a plurality of cells therein, at least one cell displaying hospital room information regarding room availability and patient occupancy in the room; said matrix displaying the plurality of cells in column form; and displaying, responsive to a user interaction with a cell in the matrix of a patient occupied hospital room, an overlay window having secondary room status information therein comprising patient specific information regarding the status of the hospital room.

For a better understanding of the present invention, together with other and further features and advantages thereof, reference is made to the following description, taken in conjunction with the accompanying drawings, and the scope of the invention will be pointed out in the appended claims.

BRIEF DESCRIPTION OF THE DRAWINGS

FIG. 1 illustrates a graphical matrix for a plurality of patient units in accordance with an embodiment of the present invention;

DETAILED DESCRIPTION

Figure 1:
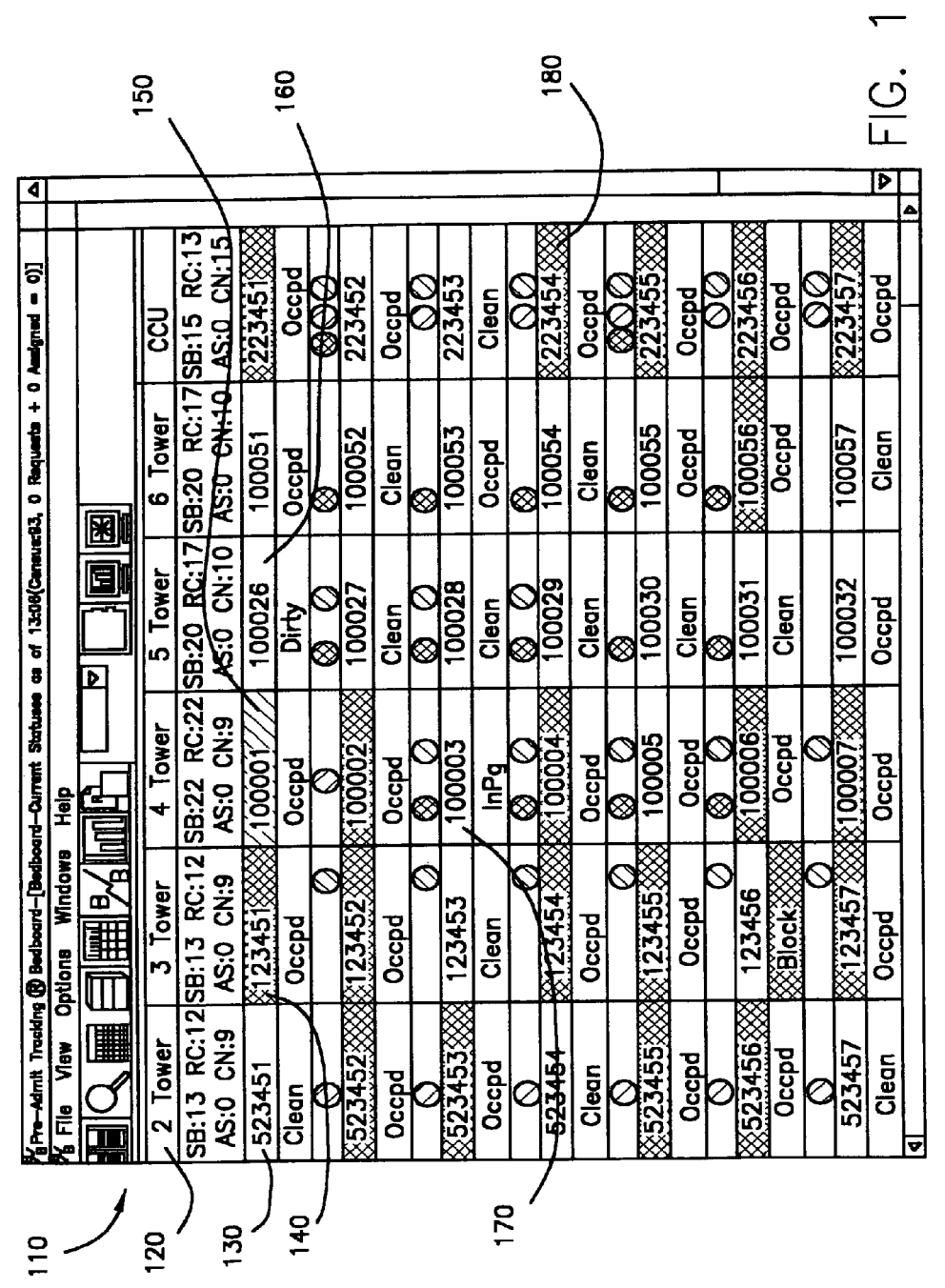
Figure 2:
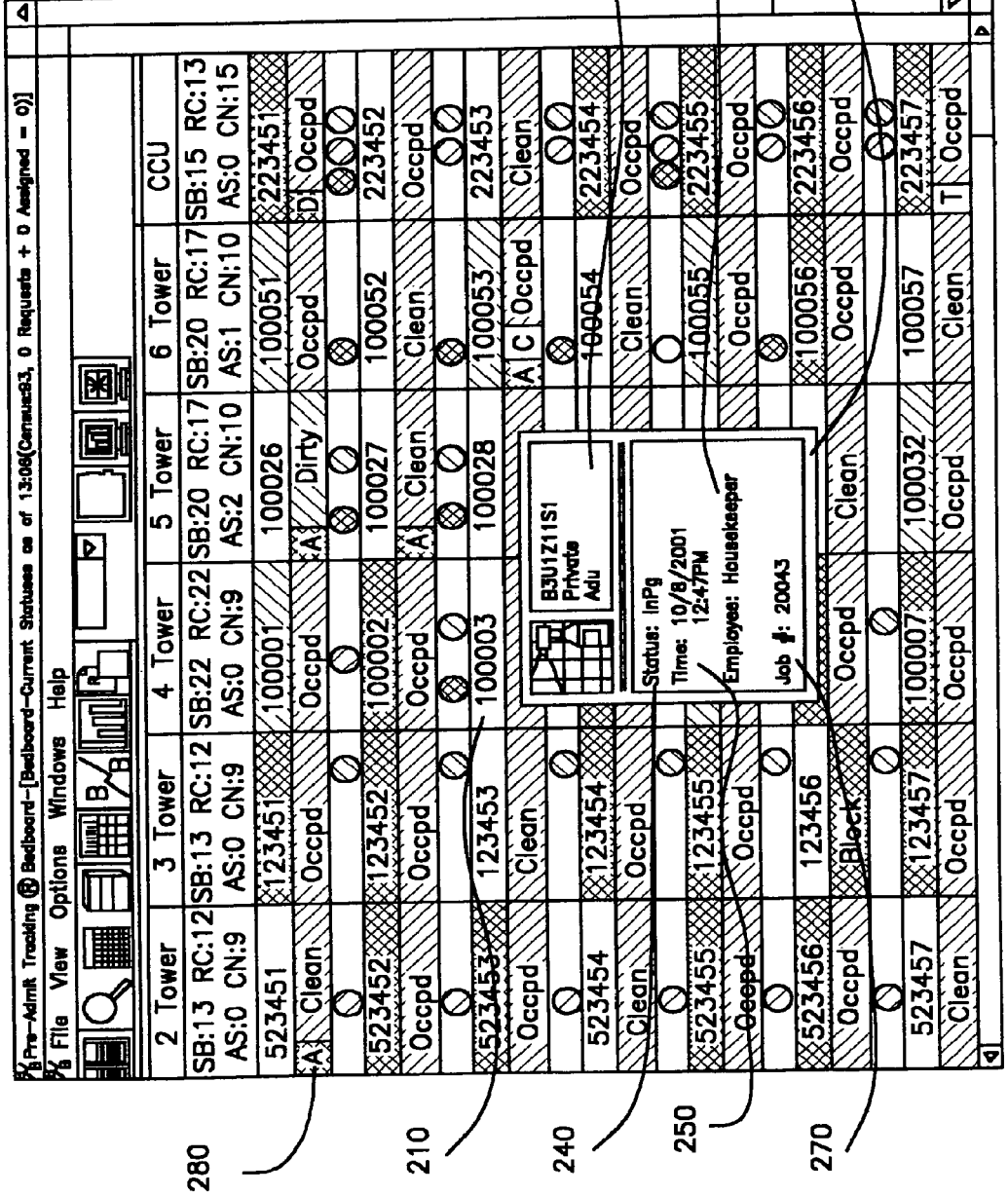
FIG. 2 illustrates the information provided when one of the patient rooms is "drilled down" in accordance with the present invention.

As shown in FIG. 1, a matrix 110 setting forth the patient rooms within various patient units within a hospital is shown. Patient units are preferably arranged in columnar form, with information about each patient unit appearing at the top of the column. For example, the first column displays information for patient unit 2 Tower. This is indicated at reference numeral 120. Other patient units shown in matrix 110 include 3 Tower, 4 Tower, 5 Tower, 6 Tower, and CCU (Critical Care Unit). Information on additional patient care units may also be displayed. Such additional patient care units may include ICU (Intensive Care Unit) and PACU (Perianesthesia Care Unit). Additional information relating to each patient care unit is also preferably displayed. As shown in matrix 110, such additional information includes the number of staffed beds (SB), the reserved capacity of the patient unit (RC), the number of assigned beds (AB), and the census now (CN). SB is the number of beds for which nursing staff currently exists to handle, RC is the number of beds available for pre-booking, that is, reserving twenty-four hours or more in advance of a scheduled admission, AB is the number of beds to which patients have been assigned, and CN is the current number of occupied beds on that unit, in other words, the "census now" on that unit.

A cell displaying information on each room preferably contains three levels. The first level preferably displays the room number. A user may optionally choose to display a bed "abbreviation" instead of the bed number in this space. The background of this portion of the cell preferably indicates the sex of the patient assigned to the bed, with blue indicating male and pink indicating female. The second level preferably shows the current status of the bed, and optionally, the "pre-admit status" of the bed. The third level preferably contains space for four user defined attributes.

Presently, the preferred set of current status (or status indicators) of a bed are: occupied, clean, in-progress, stat, next, blocked, Udef8, Udef9, and dirty. Occupied indicates a patient has been admitted to this bed. Clean indicates the bed is clean, empty and ready for a new patient. InProgress indicates a hospital employee is in the process of cleaning the bed. Stat indicates the bed is empty and dirty and needs to be cleaned immediately. Next indicates the bed is empty and dirty and should be clean as soon as possible. Blocked indicates the bed can not be used for an inpatient admission. Udef8 denotes the user has created a unique "user defined" category for this status. Udef9 denotes the user has created a unique "user defined" category for this status (which should be different than Udef8). Dirty indicates the bed is empty and needs to be cleaned.

Presently, the preferred "pre-admit status" indicators of the bed are assigned, pending discharge, pending transfer or confirmed discharge. Assigned indicates the bed has been reserved for a specific patient. Pending Discharge indicates the bed will be empty soon, as the patient is supposed to be going home. Pending Transfer indicates the bed will be empty soon as the patient is supposed to be placed in another bed in the hospital. Confirmed Discharge indicates the bed will be empty soon, and the patient will be leaving the hospital for sure.

Presently there are four preferred user defined attributes; currently contemplated examples include: whether the bed is an isolation bed, a telemetry bed, and a bed side terminal bed. While the drawings reflect the presence of a user defined attribute, the user defined attribute itself has not been defined. A user defined attribute may be any attribute which is important to a user of the present invention. The presence of a user defined attribute is also preferably shown through the use of color. In the present example, an isolation bed is indicated by red, a telemetry bed by yellow, a bed side terminal bed by green, and the remaining user defined option by light blue.

Reference numeral 130 denotes the cell for Room 523451. On the first level of this cell, the room number is displayed, with a plain background. The second level of this cell indicates the bed status (clean), and the third level indicates this bed has one predefined user selected attribute. The plain background of the first level indicates no patient is currently in this room. The background of the second level is preferably green to provide a visual indication of the status of the room. The third level indicates the bed has one of the user defined attributes, which in this case is the bed is a telemetry bed. As discussed above, preferably this indication would appear in yellow.

Reference numeral 140 denotes the cell for Room 123451. One the first level of this cell, the room number is displayed with a colored background. The second level of this cell indicates the bed status (occupied), and the third level indicates this bed has a predefined user attribute. The blue colored background of the first level indicates the patient currently in this room is a male. The background of the second level is preferably orange to provide a visual indication of the occupied status of the room. The third level indicates the bed has one of the user defined attributes, which (as discussed above), is an undefined attribute and preferably appears in light blue.

Reference numeral 150 denotes the cell for Room 100001. On the first level of this cell, the room number is displayed with a colored background. The second level of this cell indicates the bed status (occupied), and the third level indicates this bed has a predefined user attribute. The pink colored background of the first level indicates the patient currently in this room is a female. The background of the second level is preferably orange to provide a visual indication of the occupied status of the room. The third level indicates the bed has one of the user defined attributes, which in this case is the bed is a telemetry bed. As discussed above, this indication would preferably appear in yellow.

Reference numeral 160 denotes the cell for Room 100026. One the first level of this cell, the room number is displayed without a colored background. The second level of this cell indicates the bed status (dirty), and the third level indicates this bed has two predefined user attributes. The absence of a background color indicates there is no patient in this bed. The background of the second level is preferably brown to provide a visual indication of the dirty status of the room. The third level indicates the bed has two of the user defined attributes, which in this case is the bed is an isolation bed having a bed side terminal bed. As discussed above, these indications would preferably appear in red and green.

Reference numeral 170 denotes the cell for Room 100003. One the first level of this cell, the room number is displayed without a colored background. The second level of this cell indicates the bed status (in progress), and the third level indicates this bed has two predefined user attributes. The absence of a background color indicates there is no patient in this bed. The background of the second level is preferably yellow to provide a visual indication of the in progress status of the room. The third level indicates the bed has two of the user defined attributes, which in this case is the bed is an isolation bed having a bed side terminal bed. As discussed above, these indications would preferably appear in red and green.

Reference numeral 180 denotes the cell for Room 223454. One the first level of this cell, the room number is displayed with a blue background. The second level of this cell indicates the bed status (occupied), and the third level indicates this bed has three predefined user attributes. The first level blue background color indicates there is a male patient in this bed. The background of the second level is preferably orange to provide a visual indication of the in occupied status of the room. The third level indicates the bed has three of the user defined attributes, which in this case is the bed is an isolation telemetry bed having a bed side terminal bed. As discussed above, these indications would preferably appear in red, yellow, and green.

Referring now to FIG. 2, a display matrix is shown. This display matrix is similar to that shown in FIG. 1. Reference numeral 210 corresponds to reference numeral 170, and denotes the cell for Room 100003. Clicking on this cell ("drilling down") brings up secondary information about the status of the bed, which is shown at reference numeral 220. This information includes an indication at reference numeral 230, along with other information, that the room is being cleaned. At reference numeral 240 the status of the room is shown (in progress). At reference numeral 250 the time and date of the status is shown. At reference numeral 260 the employee involved in the status is indicated, and the job number is shown at reference numeral 270.

Certain second cell levels in FIG. 2 include information in addition to the status of the room. By way of example, at reference numeral 280, an "A" appears on the second level. The indicium indicates that the bed has been assigned to a patient, even though the room is not yet occupied. Currently, other preferred indicia include "D", which indicates the patient will be discharged; "C", which indicates the patient is a confirmed or more certain status of a pending discharge; and "T", which indicates a transfer is pending. Additional indicia may also be used to indicate other conditions. A room is not limited to a single indicium; one or more indicia may be used for each bed.

Figure 3:
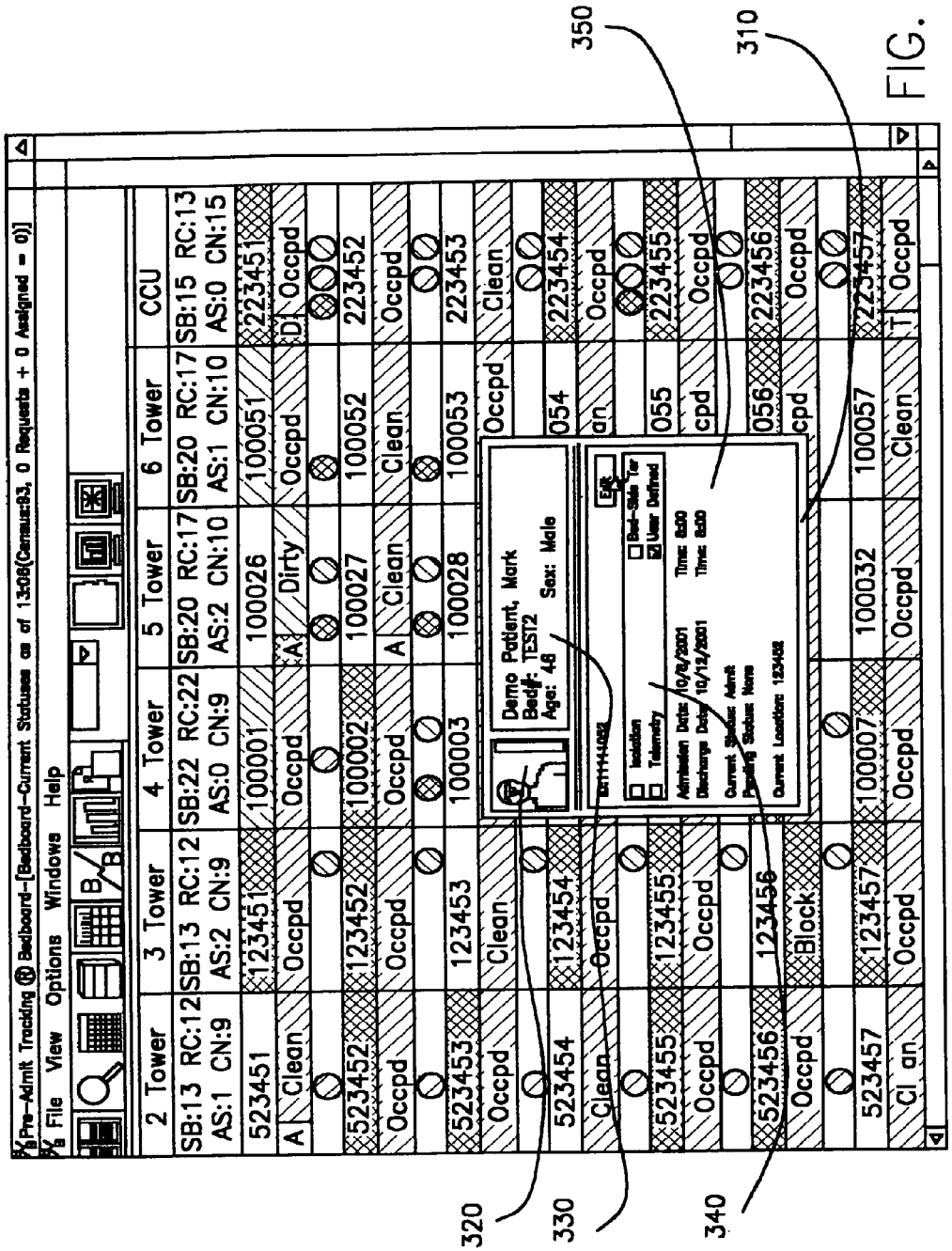
FIG. 3 illustrates the information provided when another patient room is "drilled down" in accordance with the present invention.

Referring now to FIG. 3, a display matrix is shown. This display matrix is similar to that shown in FIGS. 1 and 2. Room 123452 is shown in both of these figures. Clicking on the cell for this room also brings up secondary information about the status of the bed, which is shown at reference numeral 310. This information includes an indication at reference numerals 320 and 330, along with other information, that the room is occupied by a patient. The information displayed at reference numeral 330 includes the name of the patient, the bed number, the age of the patient, and the sex of the patient. Additional information may also be displayed.

At reference numeral 240 an indication of the attributes associated with the bed are displayed. Here "user defined" is checked, which corresponds to the bed attributes shown for this room in FIGS. 1 and 2.

At reference number 350, additional secondary information is displayed. This information includes the date and time of the patient's admission, the date and time of the patient's discharge, the current status of the patient, the pending status of the patient and the room number (current location). Additional information may also be displayed. The current status of the patient indicates the real time (present) status of the patient. Pending status of the patient is non-real time status. Presently, the preferred status indicators are similar to the "pre-admit status" indicators discussed above and include: admit, pending discharge, pending transfer or confirmed discharge. Admit indicates the patient has been admitted. Pending Discharge indicates the patient is supposed to be going home. Pending Transfer indicates the patient is supposed to be placed in another bed in the hospital. Confirmed Discharge indicates the patient will be leaving the hospital for sure.

Figure 4:
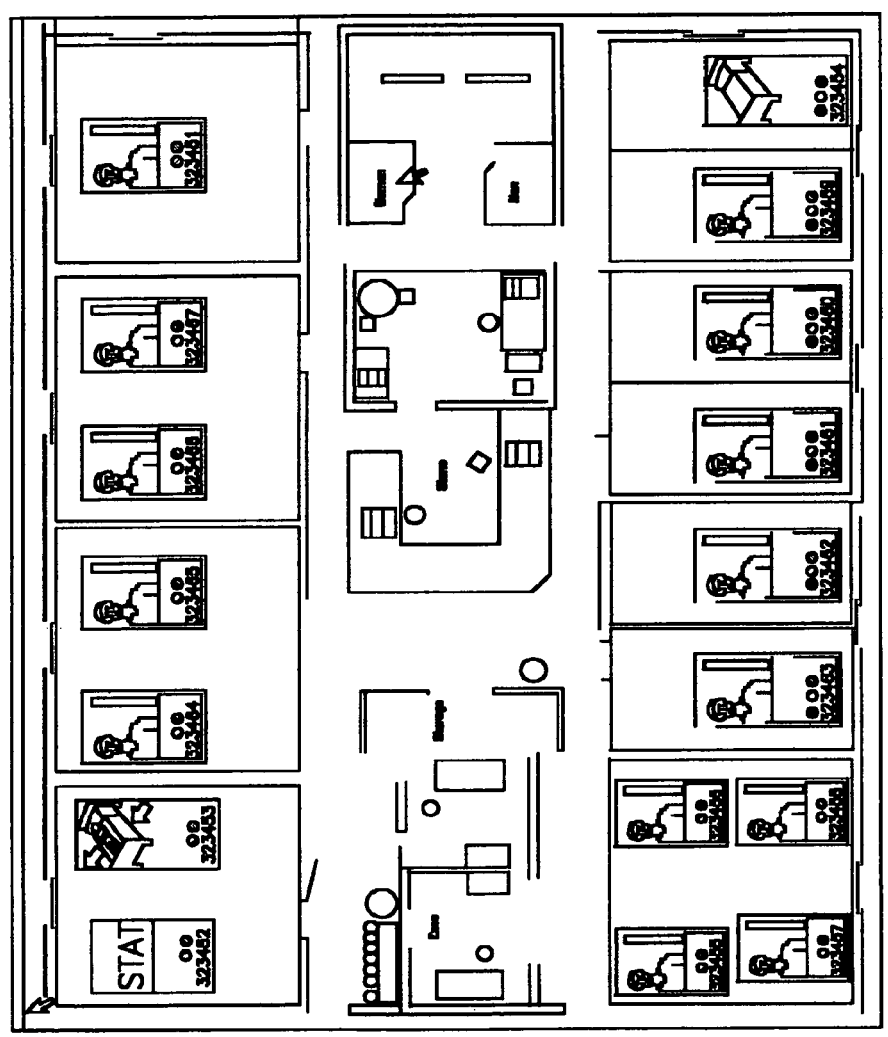
FIG. 4 illustrates a graphical depiction of a patient unit in accordance with an embodiment of the present invention.

It is presently preferred that a user of the present invention be given the option of viewing the location of a room of interest in the patient unit. Referring now to FIG. 4, a floor plan of a patient unit is shown. This permits personnel to fix the location of the room of interest. In FIG. 4, the room of interest (Room 323454) appears in the bottom right hand corner of the floor plan. The icons shown within FIG. 4 are similar to those described in U.S. patent application Ser. No. 09/567,897, filed May 10, 2000, and an icon visually depicts the status of each room of the patient unit.

It should be understood that information may be visually displayed in accordance with the present invention on a typical CRT computer monitor. It is preferred, however, to display such visual information on a flat panel monitor. It should be further understood that the patient units for which information is visually displayed in accordance with the present invention may be selected by a user of the present invention. For example, it may be desirable to view all patient units with a similar focus, for example, all cardiac units.

In recapitulation, the present invention, in accordance with at least one presently preferred embodiment, provides a manner of visually displaying information in a manner to enhance comprehension of the information. As such, it is to be understood that the present invention, in accordance with at least one presently preferred embodiment, may be utilized in environments other than hospitals, such as hotels, dorms, or any other situation where information about rooms is desired to be graphically displayed.

It is to be understood that the present invention, in accordance with at least one presently preferred embodiment, includes: a display and an arrangement for producing a matrix for being viewed on the display, the matrix comprising a plurality of cells, and each cell conveying information on a room. Together, these may be implemented on at least one general-purpose computer running suitable software programs. These may also be implemented on at least one Integrated Circuit or part of at least one Integrated Circuit. Thus, it is to be understood that the invention may be implemented in hardware, software, or a combination of both.

If not otherwise stated herein, it is to be assumed that all patents, patent applications, patent publications and other publications mentioned and cited herein are hereby fully incorporated by reference herein as if set forth in their entirety herein.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method of graphically displaying room information, comprising:
    executing, using a processor, a program of instructions in a storage device to perform steps comprising:
        displaying, on an electronic display device, a matrix view having a plurality of cells therein, at least one cell simultaneously displaying hospital room information regarding room availability and patient occupancy in the room;
        said matrix view displaying the plurality of cells in column form, wherein the matrix view displays substantially all hospital rooms of the matrix view in column form; and
        displaying, responsive to a user interaction with a cell of a patient occupied hospital room in the matrix view, a window overlaying one or more of the plurality of cells in the matrix view, the window having secondary room status information therein comprising patient specific information regarding the status of the patient occupied hospital room.

2. The method of claim 1, wherein the patient specific information is selected from the group of information consisting of patient pending discharge, patient pending transfer, and patient confirmed discharge.

3. The method of claim 1, wherein each of the plurality of cells comprises three levels.

4. The method of claim 3, wherein the three levels include:
    a first level displaying a room number;
    a second level displaying current status of a bed within a room associated with the cell; and
    a third level containing one or more user defined attributes.

5. The method of claim 1, wherein at least one column of cells comprises summary information regarding a patient care unit associated with the at least one column of cells, and wherein the summary information regarding a patient care unit associated with the at least one column of cells includes a number of staffed beds, a reserved capacity of the patient care unit, a number of assigned beds, and a census now number.

6. The method of claim 5, wherein the patient care unit includes one or more of a critical care unit and an intensive care unit.

7. The method of claim 1, wherein each cell includes textual information regarding room availability and patient occupancy of the room.

8. The method of claim 7, wherein the patient specific information regarding the status of the room comprises patient specific bed status information.

9. The method of claim 8, wherein the patient specific bed status information comprises impending bed availability information derived from the patient specific bed status information.

10. The method of claim 1, wherein the display of said secondary room status information is restricted.

11. The method of claim 1, wherein:
    one or more levels of the plurality of cells are functionally linked; and
    user interaction with one or more of the levels displays an overlay window for a cell;
    the overlay window being displayed on top of a part of the matrix view displaying the plurality of cells.

12. The method of claim 1, further comprising automatically updating the matrix view displaying the plurality of cells to include summary information in a cell based on a changing status of a room associated with the cell.

13. The method of claim 12, wherein the changing status is patient assignment to a room.

14. The method of claim 12, wherein the summary information is displayed in a level of the cell.

15. The method of claim 14, wherein the summary information alters the visual appearance of the level.

16. The method of claim 1, wherein the overlay window includes a user interface for modifying information displayed therein.

17. The method of claim 1, wherein the window overlays the cell of the patient occupied room.

18. The method of claim 1, wherein the window does not overlay the cell of the patient occupied room.

19. An apparatus, comprising:
    a storage device having a program of instructions stored therein;
    a display device; and
    a processor that executes the program of instructions to display room information on the display device, the processor acting to:
    display a matrix view having a plurality of cells therein, at least one cell simultaneously displaying hospital room information regarding room availability and patient occupancy in the room;
    said matrix view displaying the plurality of cells in column form, wherein the matrix view displays substantially all hospital rooms of the matrix view in column form; and
    display, responsive to a user interaction with a cell of a patient occupied hospital room in the matrix view, a window overlaying one or more of the plurality of cells in the matrix view, the window having secondary room status information therein comprising patient specific information regarding the status of the patient occupied hospital room.

20. A program storage device readable by machine, embodying a program of instructions executable by the machine to perform:
    displaying, on an electronic display device, a matrix view having a plurality of cells therein, at least one cell simultaneously displaying hospital room information regarding room availability and patient occupancy in the room;
    said matrix view displaying the plurality of cells in column form, wherein the matrix view displays substantially all hospital rooms of the matrix view in column form; and
    displaying, responsive to a user interaction with a cell of a patient occupied hospital room in the matrix view, a window overlaying one or more of the plurality of cells in the matrix view, the window having secondary room status information therein comprising patient specific information regarding the status of the patient occupied hospital room.

* * * * *